| United States Patent [19] | [11] 3,992,159 |
| Mitchell | [45] Nov. 16, 1976 |

[54] PROCESS FOR PURIFICATION BY CRYOGENIC SUBLIMATION

[75] Inventor: James Windfield Mitchell, Somerset, N.J.

[73] Assignee: Bell Telephone Laboratories, Incorporated, Murray Hill, N.J.

[22] Filed: June 23, 1975

[21] Appl. No.: 589,204

[52] U.S. Cl. ............................ 23/294; 23/293 R; 23/293 A; 23/295 R; 23/264; 23/252 A; 217/71; 159/DIG. 5; 260/706; 260/606.5; 34/5; 423/584; 423/300; 423/407; 423/491; 423/341; 423/489; 423/492; 260/448.8 A; 260/429 R; 260/541; 260/542

[51] Int. Cl.$^2$............................................ B01D 7/00

[58] Field of Search .......... 23/294 R, 293 R, 293 A, 23/295, 264; 423/584; 210/71; 159/DIG. 5; 260/706; 34/5

[56] References Cited

UNITED STATES PATENTS

| 2,064,468 | 12/1936 | Foster............................ 260/706 X |
| 2,852,517 | 9/1958 | Lynn................................... 260/268 |
| 2,993,764 | 7/1961 | Grulet et al......................... 23/264 |
| 3,012,860 | 12/1961 | Meeker et al..................... 423/584 |
| 3,111,461 | 11/1963 | Hickman............................. 203/72 |
| 3,276,848 | 10/1966 | Barr, Sr., et al..................... 23/294 |
| 3,422,167 | 1/1969 | Bowman et al..................... 34/5 X |
| 3,516,935 | 6/1970 | Monforte et al................. 252/62.56 |
| 3,551,533 | 12/1970 | Monforte et al..................... 264/14 |
| 3,755,530 | 8/1973 | Avila et al. .......................... 34/5 X |

*Primary Examiner*—James H. Tayman, Jr.
*Attorney, Agent, or Firm*—Walter G. Nilsen

[57] ABSTRACT

A process is described for purifying liquids by cryogenic sublimation. This process involves solidifying the liquid by reducing the temperature and pressure to below the triple point. Purification is then carried out by direct transformation from the solid to the vapor phase. Because of increased differentials in vapor pressures at the low temperature at which the procedure is carried out, this purification process is highly efficient and is also particularly suitable for liquids that are susceptible to decomposition with ordinary purification procedures requiring elevated temperatures. The procedure is also advantageous in separating azeotropes, structurally similar compounds, as well as treating flammable, hydroscopic, corrosive and fuming compounds.

15 Claims, No Drawings

PROCESS FOR PURIFICATION BY CRYOGENIC SUBLIMATION

BACKGROUND OF THE INVENTION

1. Field of the Invention

The invention involves a process for purifying liquids.

2. Description of the Prior Art

A large variety of processes are used for purifying liquids. Best known is simple distillation using a fractionating column. When the liquid is reasonably stable under ambient temperature conditions, as for example, in the case of water, petroleum products, etc., this process is not only satisfactory but often economically advantageous.

Many liquids cannot be purified to a high degree using ordinary distillation methods either because they decompose under conditions of distillation, or are azeotropes and not susceptible to separation by distillation methods. Alternative procedures are available such as the use of reduced pressures in distillation columns to reduce the boiling temperature of the liquid and the use of distillation columns made from such inert materials as Teflon and quartz. However, in many instances these alternative procedures do not give sufficient improvement for many applications. This is particularly true in situations where extreme purity is required. For example, in semiconductor processing and the production of glass fibers for optical waveguides, extremely pure products are often highly desirable, and in many cases required. Thus chemical reagents used in semiconductor processing and production of optical waveguides must exhibit levels of purity far beyond those usually obtained by conventional techniques. In such cases the distillation methods described above are often inadequate.

Of particular importance for chemical reagents used in semiconductor processing and production of optical waveguides is the removal of extremely small amounts of inorganic trace impurities. An additional problem, minor impurities can result from decomposition of the chemical reagent being purified. Purity levels of the order of less than several parts per billion are often desirable at least for certain elements. For example, in semiconductor processing where large amounts of chemical reagents are used in surface treatments, even very low concentrations of certain impurities (especially those which adversely affect the doping of the semiconductor) are highly undesirable. In optical fibers where extremely low loss is desirable, high purity chemical reagents are also important. For these reasons, a purification procedure which exhibits high efficiency under conditions of minimum decomposition is highly desirable. A particular example is hydrogen peroxide in aqueous solution which is extensively used in semiconductor processing as an oxidizing agent. Since this chemical agent may be used in large amounts on the surface of semiconductors, high purity is necessary to prevent unintentional doping and/or surface contamination of the semiconductor.

SUMMARY OF THE INVENTION

The invention involves a process for the purification of substances which are liquids at ambient temperatures and pressures. This process is particularly applicable to liquids which tend to be unstable at temperatures and pressures commonly used for purification and where extreme purification is required, such as for the production of reagent chemicals used in semiconductor processing and in fabricating glass fibers for optical waveguide. In this purification process the liquid to be purified is first reduced in temperature and pressure to below the triple point. Temperature may be reduced using various means including mechanical refrigeration. The pressure is reduced using for example mechanical pumps. The substance is then spontaneously sublimed and collected in a cooler vessel. Sublimation may be enhanced by supplying some heat to the substance being purified. This is often done by providing a heat leak (such as removing insulation) to room temperature. The inventive process has the advantage of permitting high efficiency purification under conditions which minimize the subsequent contamination of the sublimate by its containing vessel. Decomposition of the substance being purified is also minimized. In semiconductor processing certain inorganic impurities ions such as sodium, gold, iron, chromium, phosphorus, tin, antimony, boron and indium are particularly important because of their potential effect on semiconductor properties. It is often desirable in such applications to have the concentration of these ions below at least one part per million and often 100 parts or even 10 parts per billion ($10^9$) on a weight fraction basis depending on the extent of use of the purified reagent and the potentially harmful effects of the particular ion. Also, for optical fiber manufacture for optical communication systems, such ions as cobalt, iron, copper, vanadium, chromium, zinc, nickel and manganese should particularly be kept at extremely low concentrations since these ions cause absorption and other losses which are detrimental to the performance of the communication system. Concentrations of less than at least one part per million are preferred and in some cases less than 100 parts or even 10 parts per billion ($10^9$) are advantageous. To obtain greater separation of the impurities during sublimation a chelating agent or ion exchange resin may be added. This procedure results in purification of liquids without the danger of decomposition and in many cases impurity levels of less than several parts per billion or less can be obtained.

DETAILED DESCRIPTION

Described below is a general procedure for carrying out the inventive process. Various kinds of apparatus may be used depending on the amount of substance to be purified and the temperature and pressure at which the procedure is carried out. For example, for substances whose triple point lies at very low temperatures, considerable insulation and refrigeration capacity may be required. To adjust separation efficiency temperature is controlled at a suitable value below the triple point. Throughput is regulated by the design of the apparatus and rate of evacuation. Although the apparatus may be made from a large variety of materials, it is often preferred to use materials which will minimize possible contamination. Thus apparatus made of quartz and Teflon as well as other low contamination materials are preferred.

Various means may be used for reducing the pressure including absorption pumps but under usual commercial manufacturing conditions a mechanical pump is preferred for convenience and economy. Caution should be taken to exclude vapors from the mechanical pump usually by means of a cold trap or trap using highly absorbing material. Temperature may also be reduced in a variety of ways including the use of cryogenic substances such as dry ice and liquid nitrogen, but under usual manufacturing conditions the use of mechanical refrigeration equipment is preferred.

After reducing the pressure and temperature to below the triple point of the substance to be purified sublimation is begun. To provide the latent heat of conversion from solid to vapor it is often preferred to incorporate a source of heat near the solid. Also, a particular temperature distribution is advantageously maintained in the apparatus so that sublimed material will be brought to the collection vessel without solidification on intermediate surfaces. In commercial processes, this may be done by proper design of the thermal insulation equipment. Heat sources such as infrared lamps and resistive heaters are also useful. The substance being purified by sublimation is collected in another vessel usually by maintaining this vessel at a lower temperature than the remaining parts of the apparatus.

A variety of substances may be purified using this technique including hydrogen peroxide, phosphorus oxychloride, acetic acid, formic acid and hydrazine. Other substances advantageously purified by this procedure and used particularly in semiconductor manufacture are arsenic trichloride, silicon tetrabromide, arsenic trifluoride, tungsten hexafluoride, and titanium tetrabromide. These substances in addition to being useful in semiconductor processing also are highly susceptible to reaction with water vapor and tend to be difficult to purify because of decomposition. In addition, organic peroxides of various kinds are difficult to purify because of instability and are prime candidates for purification by the above procedure. Certain substances used in the preparation of high purity glass for use in the production of optical waveguides are also prime candidates for purification by the inventive procedure. These substances include tetramethoxy silane, trimethoxy boron, tetramethoxy germanium, silicon tetrabromide, silicon tetrachloride and germanium tetrachloride.

In order to evaluate the efficiency of this purification procedure, the sublimation process was carried out using hydrogen peroxide as the substance to be purified. The procedure was carried out by deliberately doping an extremely pure 15 percent aqueous solution of hydrogen peroxide with certain elements whose concentration could be measured at very low levels. Initial experiments were carried out by doping the hydrogen peroxide with 1 microgram/milliliter each of the ions, iron, cobalt, chromium, vanadium, nickel, manganese and copper. The sublimation procedure described above was carried out on 50 milliliters of solution.

The temperature and pressure of the aqueous hydrogen peroxide was reduced to below the triple point by cooling the peroxide with a dry ice-acetone mixture and reducing the pressure with a vacuum pump. A heat lamp was used to control the sublimation rate. The peroxide was collected in a vessel cooled in a mixture of dry ice and acetone. The collected hydrogen peroxide was then analyzed using an x-ray fluroescence procedure. The peroxide collected at the end of the sublimation procedure had a volume of 45 milliliters. The concentrations of the elements deliberately added were all below the detection limit of the x-ray fluorescence analysis procedure (less than 0.1 micrograms per 10 ml sample). These results show that the decontamination factors obtained by this process were at least 100. Considering the extremely low concentration ranges involved, these are exceptionally significant decontamination factors.

In order to obtain even more sensitive results in the determination of the decontamination factors, 10 milliliters of a 15 percent aqueous solution of hydrogen peroxide which had been doped with 1 microgram/milliliter of iron, cobalt, copper, nickel, vanadium, manganese, and chromium were also spiked with cobalt 60, chromium 51, iron 59, and manganese 54. This sample then exhibited a total gamma-ray count rate of $8.18 \times 10^5$ c/min from all photopeaks of these isotopes. After a single stage of sublimation 8.7 milliliters of purified hydrogen peroxide was recovered. The $\gamma$-ray activity of this product was 7 counts per minute indicating that less than $2 \times 10^{-5}$ of the original iron, cobalt, chromium, and manganese remained in the purified fraction. This indicates that only an average of approximately 2 parts per billion of each impurity remained in the purified hydrogen peroxide. Further measurements were carried out using neutron activation. These results indicated decontamination factors of 1100, 2700 and 325 for elements, manganese, cobalt, and arsenic, respectively. These results show that the sublimation procedure described above is highly efficient for carrying out purifications at low contamination levels on substances which are liquids at ambient temperatures and might possibly be subject to decomposition when purified by standard procedures.

Sublimation was carried out on several other substances including acetic acid, formic acid, ammonium hydroxide, hydrazine, arsenic trichloride, and tungsten hexafluoride. It was shown that these substances sublime readily and are prime candidates for purification by the inventive process.

Another advantage of the sublimation procedure is the fact that this purification process can be carried out in combination with another procedure for greatly reducing the concentration of chemical entities such as inorganic ions. This procedure involves using non-volatile chelating agents and/or ion exchange resins to bind the inorganic ions chemically in a non-sublimable matrix, which remains as a residue during the sublimation procedure. The significant advantage of the combined purification procedure is associated with the low temperature at which the sublimation is carried out, and the extreme efficiency of retention of potentially sublimable traces. Depending on the chemical nature of the liquid prior adjustment of pH may be necessary to use chelating agents or ion exchange resins effectively in the purification process. Also under the conditions of the purification procedure there is little or no chance of the chelating compound or ion exchange resin decomposing to give sublimable products that would contaminate the purified sublimate. Using this procedure extremely high decontamination factors are obtained at extremely low concentrations of inorganic ions.

A large variety of chelating agents may be used. A particular one preferred because of its availability and strong chelating characteristics is ethylene diamine tetraacetic acid (EDTA). A large variety of ion exchange resins may be used. Strongly basic anionic exchange resins and strongly acidic cationic exchange resins are preferred because of their strong affinity for the ions which are to be removed form the substance being purified. Certain exchange resins with quaternary ammonium exchange groups attached to a styrene-divinylbenzene polymer lattice are strongly basic anionic exchange resins. Particular quaternary ammonium exchange groups that form strongly basic anionic resins are trimethyltolyl ammonium chloride, dimethyltolyl (hydroxy) ethyl ammonium chloride and resins containing pyridinium exchange groups. Examples of strongly acidic cation exchange resins suitable for use in this purification procedure are resins composed of sulfonic acid exchange groups attached to a styrene-divinylbenzene polymer lattice. Also particularly useful are chelating ion exchange resins such as styrene-divinylbenzene copolymers containing imminodiacetate functional groups. These chelating agents and ion exchange resins are particularly useful for increasing the retention of not only relatively large amounts of inorganic impurities but also for retaining extremely low concentrations of certain potentially volatile undesirable inorganic ions.

This procedure may also be useful in separating azeotropic mixtures of volative inorganic halides. Also in the separation of compounds exhibiting very close boiling temperatures, the sublimation procedure might be extremely useful especially if the solid-vapor equilibrium curve happens to be somewhat different for the compounds being separated. A particular situation might be the separation of isomeric compounds often having close boiling points but possibly somewhat different solid-vapor equilibrium curves. The procedure is ideally suited to the purification of highly unstable compounds such as organic peroxides. Highly flammable or corrosive compounds are also advantageously purified using the inventive procedure. Inert atmospheres such as nitrogen, argon, helium, etc., may also be used in conjunction with the inventive procedure.

What is claimed is:

1. A process for the purification of substances which are liquids at ambient temperatures and pressures by phase transformations between different states of matter of the substance so as to leave impurities in the residue and collecting a purified substance, in which the process includes the steps of
   a. reducing the temperature and pressure of the substance being purified from ambient temperatures and pressure to below the triple point of the substance being purified using cooling means and pressure reducing means,
   b. carrying out the phase transformation between states of matter of the substance being purified from solid state to vapor state,
   c. collecting the purified substance in a collection vessel, and
   d. increasing the temperature and pressure of the purified substance to ambient temperatures and pressures so as to return the purified substance to the liquid state.

2. The process of claim 1 in which the cooling means is mechanical refrigeration apparatus.

3. The process of claim 1 in which the pressure reducing means is mechanical vacuum pump apparatus.

4. The process of claim 1 in which the impurities are at least one ion selected from the group consisting of sodium, gold, iron, aluminum, chromium, phosphorus, tin, antimony, boron and indium, with the concentrations of these ions in the purified substance less than one part per million by weight.

5. The process of claim 4 in which the concentration of these ions in the purified substance is less than 100 parts per billion by weight.

6. The process of claim 1 in which the residue ions are selected from the group consisting of copper, vanadium, zinc, nickel, cobalt, and manganese and in which the concentration of these ions in the purified substance is less than one part per million by weight.

7. The process of claim 6 in which the concentration of these ions is less than 100 parts per billion by weight.

8. The process of claim 1 in which a heat source is provided to supply the latent heat of conversion from solid to vapor and to prevent condensation on unwanted parts of the sublimation apparatus.

9. The process of claim 1 in which the substance to be purified is selected from the group consisting of hydrogen peroxide, phosphorous oxychloride, acetic acid, formic acid and hydrazine.

10. The process of claim 1 in which the substance to be purified is useful in semiconductor processing and is selected from the group consisting of arsenic trichloride, silicon tetrabromide, arsenic trifluoride, tungsten hexafluroide and titanium tetrabromide.

11. The process of claim 1 in which the substance to be purified is useful in the manufacture of glass fibers and are selected from the group consisting of tetramethoxy silane, trimethoxy boron, tetramethoxy germanium, silicon tetrachloride and germanium tetrachloride.

12. The process of claim 1 in which prior to reducing the temperature and pressure of the substance below its triple point the process has the additional step of adding a chelating agent to the substance being purified to chemically tie impurities to the chelating agent and prevent sublimation of the impurities.

13. The process of claim 1 in which prior to reducing the temperature and pressure of the substance below its triple point, the process has the additional step of adding an ion exchange resin to the substance being purified to chemically tie impurities to the chelating agent and prevent sublimation of the impurities.

14. The process of claim 1 in which prior to reducing the temperature and pressure of the substance below its triple point the process has the additional step of adding both a chelating agent and an ion exchange resin to the substance being purified to chemically tie impurities to the chelating agent and prevent sublimation of the impurities.

15. The process of claim 1 in which prior to reducing the temperature and pressure of the substance below its triple point the process has the additional step of adding a chelating ion exchange resin to the substance being purified to chemically tie impurities to the chelating agent 6 and prevent sublimation of the impurites.

* * * * *